United States Patent [19]

Johns et al.

[11] Patent Number: 5,681,558
[45] Date of Patent: Oct. 28, 1997

[54] METHOD OF USING BETA-INTERFERONS TO TREAT RESTENOSIS

[75] Inventors: Anthony Johns, Hercules; Robert J. Mintzer, Pinole, both of Calif.

[73] Assignee: Berlex Laboratories, Inc., Richmond, Calif.

[21] Appl. No.: 565,701

[22] Filed: Nov. 30, 1995

[51] Int. Cl.$^6$ ............................................. A61K 38/21
[52] U.S. Cl. ............................................. 424/85.6
[58] Field of Search ................................. 424/85.6

[56] References Cited

U.S. PATENT DOCUMENTS

| | | |
|---|---|---|
| 4,462,940 | 7/1984 | Hanisch et al. |
| 4,588,585 | 5/1986 | Mark et al. |
| 4,992,271 | 2/1991 | Fernandes et al. |

OTHER PUBLICATIONS

Foley et al., "Prevention of Restenosis After Coronary Balloon Angioplasty: Rationale and Design of the Fluvastatin Angioplasty Restenosis (FLARE) Trial," *American Journal of Cardiology*, (1994) 73:50D–61D.

Palmer et al. "Interferon–β A Potential Autocrine Regulator of Human Vascular Smooth Muscle Cell Growth", *Laboratory Investigation*, (1992) 66(6):715–721.

Hammar, et al. "Induction of Tubuloreticular Structures in Cultured Human Endothelial Cells by Recombinant Interferon Alfa and Beta." *Ultrastructural Pathology*. (1992) 16:211–218.

Dupont et al. "Regulation of Xanthine Dehydrogenase and Xanthine Oxidase Activity and Gene Expression in Cultured Rat Pulmonary Endothelial Cells," *J. Clin. Invest.* (1992) 89:197–202.

Ruszczak et al. "Effects of rIFN Alpha, Beta and Gamma on the Morphology, Proliferation, and Cell Surface Antigen Expression of Human Dermal Microvascular Endothelial Cells In Vitro", *Journal of Investigative Dermatology*, (1990) 95(6):693–699.

Warner et al., "Immune Interferon Inhibits Proliferation and Induces 2'–5'–Oligoadenylate Synthetase Gene Expression in Human Vascular Smooth Muscle Cells," *J. Clin. Invest.*, (1989) 83:1174–1182.

Fukumoto et al. "Independent inhibition of DNA Synthesis by Protein Kinase c, Cyclic AMP and Interferon α/β in Rabbit Aortic Smooth Muscle Cells," *Biochemical and Biophysical Research Communications*, (1988) 157(1):337–345.

*Primary Examiner*—Chhaya D. Sayala
*Attorney, Agent, or Firm*—Carol J. Roth

[57] ABSTRACT

The use of human interferon-β to treat or prevent coronary restenosis is described herein.

5 Claims, 4 Drawing Sheets

The effect of Betaseron (1000 IU/mL in 5.0% fetal bovine serum) on the growth of human coronary endothelial cells (o-o) versus untreated human coronary artery endothelial cells (•-•).

The effect of Betaseron (1000 IU/mL in 5.0% fetal bovine serum) on the growth of human coronary smooth muscle cells (o-o) versus untreated human coronary artery smooth muscle cells (•-•).

The effect of Betaseron (in 5.0% fetal bovine serum) on thymidine incorporation into human coronary smooth muscle cells (●-●) versus thymidine incorporation into human coronary endothelial cells (o-o).

| CELL TYPE | STRAIN # | DONOR AGE/SEX | THYMIDINE INCORPORATION (% CONTROL) |
|---|---|---|---|
| CORONARY SMC | 3016 * | 3/M | 27 |
| CORONARY SMC | 3033 * | 38/F | 40 |
| CORONARY SMC | 3011 * | 32/M | 17 |
| CORONARY SMC | 2896 * | 61/F | 97 |
| CORONARY SMC | 2851 | 64/M | 73 |
| CORONARY SMC | 2603 | 48/M | 42 |
| CORONARY SMC | 3003 | 50/F | 36 |
| CORONARY EC | 3016 * | 3/M | 69 |
| CORONARY EC | 3033 * | 38/F | 97 |
| CORONARY EC | 3011 * | 32/M | 101 |
| CORONARY EC | 2896 * | 61/f | 112 |

* MATCHED SMC & EC

The effect of Betaseron (1000 IU/mL in 5.0% fetal bovine serum) on thymidine incorporation into human coronary smooth muscle cells and human coronary endothelial cells.

FIGURE 4

METHOD OF USING BETA-INTERFERONS TO TREAT RESTENOSIS

FIELD OF THE INVENTION

The present invention is directed to the use of native or recombinant human interferon-β, particularly Betaseron, in treating restenosis in humans, particularly coronary restenosis.

BACKGROUND OF THE INVENTION

Coronary restenosis is a narrowing of the coronary artery at the site of vascular injury following transluminal coronary balloon angioplasty. It can also occur following endarterectomy and arteriectomy. Although the exact interactions of the factors contributing to coronary restenosis are continuing to be clarified, the identifying characteristic is the proliferation of normally quiescent coronary smooth muscle cells at the site of injury of the coronary arterial wall following the surgical procedure. During this period, endothelial cells in the arterial wall are also proliferating in order to restore an intact luminal endothelial surface. Accordingly, an ideal profile for a compound for the prevention of coronary restenosis would be a compound that inhibited the growth of the smooth muscle cells with either no effect or a stimulatory effect on the proliferation of the endothelial cells.

Interferons are part of the body's natural defense mechanisms. They are known to possess antiviral, antitumor and immunoregulatory properties and are species specific in their utility and function. Type I interferons include interferon-α and interferon-β. Type II interferons include interferon-γ. Human interferon-β is available as a naturally produced product from human fibroblasts and as a recombinant product. Of particular interest is the type of recombinant human interferon-β known commercially in the United States as Betaseron (interferon-$β_{ser17}$), which is disclosed in U.S. Pat. No. 4,588,585 (Cetus Corporation) as being useful in regulating cell growth in humans, in treating viral diseases and in stimulating natural killer cell activity.

Human interferon-β has been shown to decrease proliferation (which was induced by serum) in human saphenous vein smooth muscle cells (Palmer et al., *Laboratory Investigation* (1992), Vol. 66, No. 6, pp. 715–721); and rabbit interferon α/β has been shown to decrease proliferation in rabbit aortic smooth muscle cells (Fukumoto et al., *Biochemical and Biophysical Research Communications* (1988), Vol. 257, No. 1, pp. 337–345).

Human interferon-α and human interferon-β has been shown to be antiproliferative in human dermal microvascular endothelial cells in vitro (Ruszczak et al., *J. Invest. Dermatol.* (1990), Vol. 95, pp. 693–699), and to increase tubuloreticular structure formation in cultured human endothelial cells (Hammer et al., *Ultrastructure Pathol.* (1992), Vol. 16, pp. 211–218). Rat interferon-α/β has been shown to have no effect on proliferation of cultured rat pulmonary endothelial cells (Dupont et al., *J. Clin. Invest.* (1992), Vol. 89, pp. 197–202).

It has now been discovered that human interferon-β, particularly Betaseron, is effective in treating coronary restenosis in humans by selectively inhibiting the proliferation of coronary smooth muscle cell at the site of vascular injury following a surgical procedure while having no inhibitory effect on the normal proliferation of coronary endothelial cells following the procedure.

SUMMARY OF THE INVENTION

The present invention is directed to methods for treating coronary restenosis by administering a therapeutically effective amount of an interferon-β to a human in need thereof. In particular, this invention is directed to methods for treating coronary restenosis by administering a therapeutically effective amount of a human interferon-β to a human in need thereof wherein the human interferon-β selectively inhibits or prevents the proliferation of coronary smooth muscle cells at a site of vascular injury as a consequence of transluminal coronary balloon angioplasty, endarterectomy or arteriectomy while having no inhibitory effect on the proliferation of coronary endothelial cells. Preferably, the interferon-β used in the methods of the invention is Betaseron, i.e., interferon-$β_{ser17}$, which is produced by recombinant means.

In addition, this invention is directed to a method of inhibiting the proliferation of human coronary smooth muscle cells while having no inhibitory effect on coronary endothelial cells in vitro or in vivo by the administration of human interferon-β, preferably interferon-$β_{ser17}$.

BRIEF DESCRIPTION OF THE DRAWINGS

FIG. 4 is a table demonstrating the effect of Betaseron (1000 IU/mL) on thymidine incorporation in different human cell types and strains (each strain is an individual).

DETAILED DESCRIPTION OF THE INVENTION

Definitions

Figure 1:
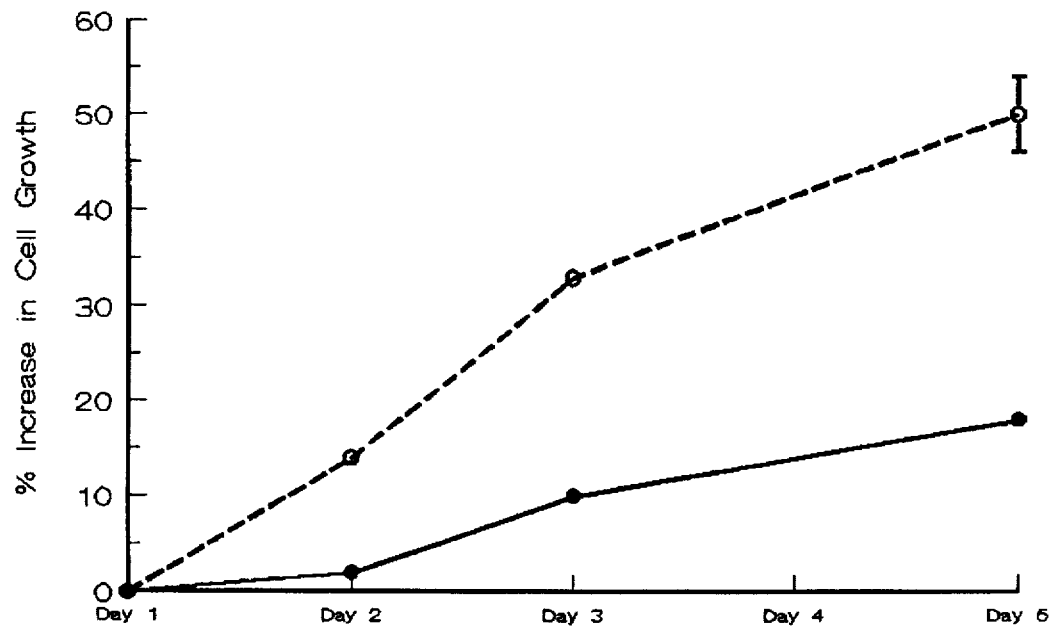
FIG. 1 is a graph demonstrating the effect of Betaseron (1000 IU/mL) on the growth of coronary endothelial cells.

As used in the specification and appended claims, unless specified to the contrary, the following terms have the meaning indicated:

"Interferon-β" or "β-interferons" includes native and recombinant Type I interferons exhibiting the same or similar pharmaceutical characteristics as the Type I interferons commonly known as interferon-β-1a and interferon-β-1b.

"Interferon-α/β" refers to a unspecified mixture of Type I interferon-α and interferon-β, for example, rat interferon-α/β.

"Betaseron" refers to the recombinantly produced human interferon-β wherein the cysteine residue at the 17 position has been replaced by serine, i.e., interferon-$β_{ser17}$, as disclosed and claimed in U.S. Pat. No. 4,588,585, the disclosure of which is incorporated herein in full.

"Therapeutically effective amount" refers to that amount of human interferon-β, particularly, Betaseron, which, when administered to a human in need thereof, is sufficient to effect treatment, as defined below, for restenosis, particularly coronary restenosis. The amount of human interferon-β which constitutes a "therapeutically effective amount" will vary depending on the human interferon-β used, the severity of the restenosis, and the age and body weight of the human to be treated, but can be determined routinely by one of ordinary skill in the art having regard to his own knowledge and to this disclosure.

"Treating" or "treatment" as used herein cover the treatment of restenosis, particularly coronary restenosis, in a human, which restenosis is alleviated by the prevention or inhibition of proliferation of coronary smooth muscle cells at the site of vascular injury following angioplasty, endarterectomy or arteriectomy.

Demonstration of Utility and Administration

A. Demonstration of Utility

The present invention is directed to methods for treating or preventing restenosis, particularly coronary restenosis, by administering a therapeutically effective amount of a human interferon-β to a human in need thereof. In particular, this invention is directed to the method of using Betaseron to treat or prevent coronary restenosis. This utility was demonstrated by in vitro assays which measured a) the incorporation of thymidine (a necessary component of cell proliferation) into the appropriate cells, for example, coronary smooth muscle cell and coronary endothelial cells, by the determination of the acid-insoluble $^3$H-thymidine present in the cells following stimulation with serum in the presence or absence of different concentrations of Betaseron; and b) growth of the appropriate cells in response to the presence or absence of a certain amount of Betaseron over time using, for example, the methylene blue method or the Coulter counter method. The results of the assays, as illustrated in FIGS. 1 to 4, demonstrate the ability of Betaseron to inhibit the proliferation of human coronary smooth muscle cells while having no inhibitory effect on the proliferation of coronary arterial endothelial cells.

B. Administration

Administration of human interferon-β, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and the human interferon-β as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a human interferon-β, and 99% to 1% by weight of a suitable pharmaceutical excipient. Preferably, the composition will be about 5% to 75% by weight of a human interferon-β, with the rest being suitable pharmaceutical excipients.

The preferred route of administration is parenterally, using a convenient daily dosage regimen which can be adjusted according to the degree of severity of the restenosis to be treated. For such parenteral administration, a pharmaceutically acceptable composition containing a human interferon-β may be formed by the methods disclosed in U.S. Pat. Nos. 4,462,940, 4,588,585 and 4,992,271.

In general, a therapeutically effective daily dose of interferon-β useful for treating restenosis is 0.25 mg (8 million IU) injected subcutaneously every other day.

The following specific examples are provided as a guide to assist in the practice of the invention, and are not intended as a limitation on the scope of the invention. The cells used in the following examples were human coronary smooth muscle cells and human coronary endothelial cells obtained from Clonetics, Inc. in San Diego, Calif.

EXAMPLE 1

The following in vitro assay was conducted to illustrate the effect of Betaseron on the incorporation of thymidine in certain cells (see, e.g., "Cell Culture for Biochemists", R. L. P. Adams, Elsevier Science Publishers B.V., Amsterdam, The Netherlands, 1985).

1) Cells were seeded into 24-well plates at a density of 25,000 cells/well in their ordinary growth media (1 mL/well). The cells were left to grow to 75% confluency (this took approximately 72 hours) in a 37° C., 5% $CO_2$ incubator.

2) The growth media was then replaced with basal media (no serum or growth factor supplements), 1 mL/well. The cells were then incubated for 48 hours under these conditions.

3) The basal media was then replaced with fresh basal media (1 mL/well) which had been supplemented with 5% FBS (fetal bovine serum), 2 µCi/mL $^3$H-thymidine (Amersham cat. #TRA61), and non-radioactive thymidine resulting in a total thymidine concentration of 2 µM.

4) Immediately after the previous step, Betaseron was introduced in the appropriate vehicle, not exceeding 10 µl added per well.

5) The cells were then incubated 48 hours.

6) The cells were then washed twice (1 mL/wash) with ice-cold PBS (phosphate buffered saline), followed by two washes (1 mL/wash) in ice-cold 10% TCA (trichloroacetic acid). Each TCA wash was allowed to remain on the cells for 5 minutes. This was followed by one wash (1 mL/well) in ice-cold 100% ethanol. The ethanol was then removed and the cells were allowed 10 minutes to dry.

7) 500 µl 1N KOH was added to each well. The plates were then agitated approx. 2 hours at ambient temperature. Cells were then inspected by microscopy to confirm that they had dissolved.

8) The KOH/cell extracts were then transferred to scintillation vials containing 4.5 mL Aquasol-2 scintillant (Dupont).

9) 500 µl 1N $CH_3COOH$ was added to each well, and the resulting mixture was transferred to the corresponding scintillation vial.

10) The scintillation vials were capped, shaken to clarity, and the amount of $^3$H-thymidine present was determined by liquid scintillation spectrometry.

Figure 3:
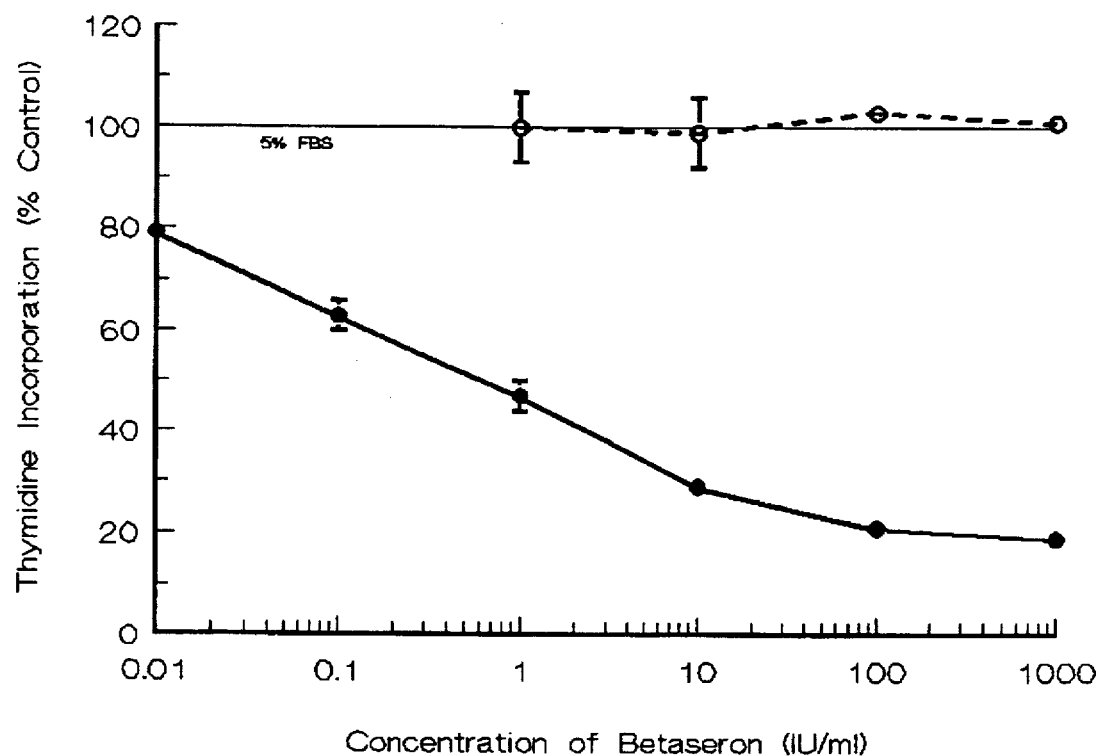
FIG. 3 is a graph demonstrating the effect of Betaseron on thymidine incorporation into human coronary smooth muscle cells and human coronary endothelial cells.

Human coronary smooth muscle cells and human coronary endothelial cells from various individuals (each individual designated as a "strain") were tested in this assay, the results of which are illustrated in FIGS. 3 and 4. As the results demonstrated, Betaseron inhibited the proliferation of coronary smooth muscle cells of a strain (i.e., an individual) and had no effect or a stimulatory effect on the proliferation of coronary endothelial cells from the same strain.

EXAMPLE 2

The following in vitro assay was conducted to illustrate the effect of Betaseron on the growth of certain cell lines (see, e.g., "A Rapid and Convenient Assay for Counting Cells Cultured in Microwell Plates: Application for Assessment of Growth Factors", *Journal of Cell Science* (1989), Vol. 92, pp. 513–518).

1) Cells of the tissue to be tested were seeded into 24-well plates at a density of 10,000 cells/well in their ordinary growth media (1 mL/well). The cells were then incubated 24 hours in a 37° C., 5% $CO_2$ incubator.

2) The growth media was then replaced with basal media (no serum or growth factor supplements) (1 mL/well). The cells were then incubated for 48 hours under these conditions.

3) The basal media was then replaced with fresh basal media (1 mL/well) which had been supplemented with 5% FBS (fetal bovine serum).

4) Immediately after the previous step, Betaseron was introduced (in the appropriate solvent) to each well, not exceeding 10 µl per well.

5) The cells were then incubated 1 to 5 days, each day terminating the growth of a complete set of treated and control cells. Termination was achieved by washing the cells once with 1 mL PBS (phosphate buffered saline), followed by addition of buffered 10% formalin (1 mL/well). The formalin was left in the wells, and the plates were stored at 0° to 5° C. until the end of the assay.

6) After the last plate had been fixed, all plates were subjected to removal of the formalin, and one wash in 10 mM borate buffer, pH 8.5 (1 mL/well).

7) Methylene blue (250 µL, 1%) in 10 mM borate buffer, pH 8.5, was added to each well and left for 30 minutes at ambient temperature.

8) The methylene blue was then removed, and the cells were given three washes in 10 mM borate buffer, pH 8.5 (1 mL/well).

9) The methylene blue retained by the cells was eluted by addition of 500 µL of 50% ethanol/50% 0.1N HCl to each well. The plates were then agitated 5 minutes at ambient temperature.

10) Methylene blue/cell extract (200 µL) was removed from each well and transferred to a 96-well microtiter plate.

11) Absorbance (650 nm) was read on a platereader.

Figure 2:
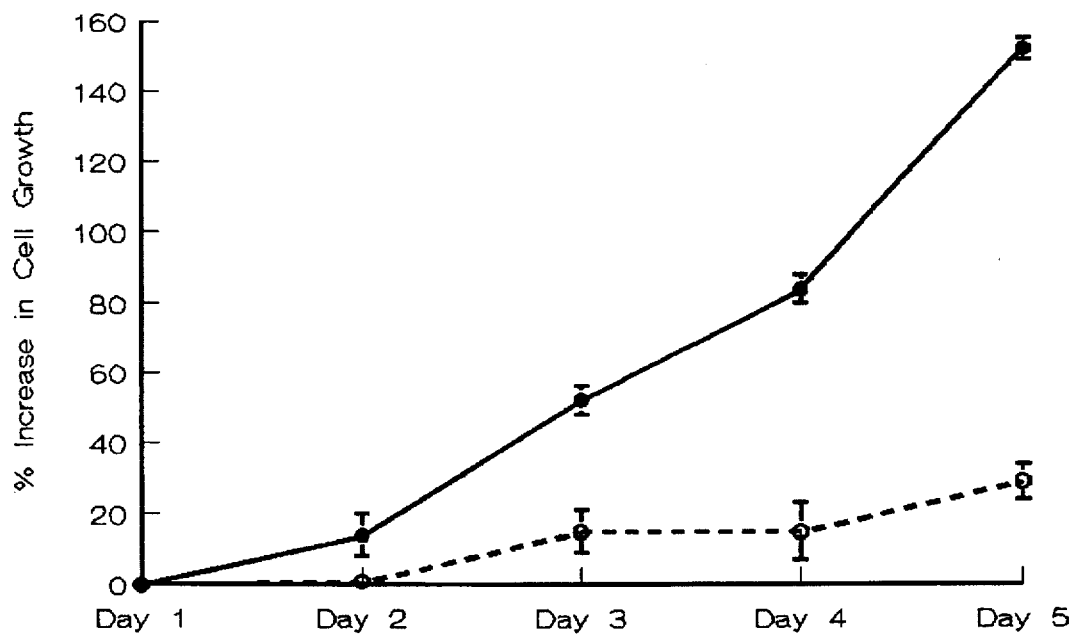
FIG. 2 is a graph demonstrating the effect of Betaseron (1000 IU/mL) on the growth of coronary smooth muscle cells.

Human coronary smooth muscle cells and human coronary endothelial cells were tested in this assay, the results of which are illustrated in FIGS. 1 and 2. As the results demonstrated, Betaseron had no effect or had a stimulatory effect on the growth of human coronary endothelial cells from one strain and had an inhibitory effect on the growth of coronary smooth muscle cells from the same strain.

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for treating restenosis which comprises administering to a human in need thereof a therapeutically effective amount of a human interferon-$\beta$.

2. The method of claim 1 wherein the restenosis is in the coronary artery.

3. The method of claim 1 wherein the human interferon-$\beta$ is interferon-$\beta_{ser17}$.

4. The method of claim 1 wherein the human interferon-$\beta$ inhibits the proliferation of coronary smooth muscle cell at the site of vascular injury following angioplasty, endarterectomy or arteriectomy.

5. A method of treating coronary restenosis which comprises administering to a human in need thereof a therapeutically effective amount of interferon-$\beta_{ser17}$ wherein the interferon-$\beta_{ser17}$ inhibits the proliferation of coronary smooth muscle cell while having no inhibitory effect on the proliferation of coronary endothelial cells.

* * * * *